United States Patent
Saito

(10) Patent No.: US 8,049,152 B2
(45) Date of Patent: Nov. 1, 2011

(54) LIGHT IRRADIATION APPARATUS AND OPTICAL MEMBER HAVING MULTIPLE REFLECTING SECTIONS AND AN ANTIREFLECTION FILM

(75) Inventor: Mitsuru Saito, Kyoto (JP)

(73) Assignee: CCS, Inc., Kyoto, Kyoto (JP)

( * ) Notice: Subject to any disclaimer, the term of this patent is extended or adjusted under 35 U.S.C. 154(b) by 509 days.

(21) Appl. No.: 12/064,702

(22) PCT Filed: Aug. 24, 2006

(86) PCT No.: PCT/JP2006/316608
§ 371 (c)(1),
(2), (4) Date: Apr. 10, 2009

(87) PCT Pub. No.: WO2007/023894
PCT Pub. Date: Mar. 1, 2007

(65) Prior Publication Data
US 2009/0302204 A1      Dec. 10, 2009

(30) Foreign Application Priority Data
Aug. 26, 2005   (JP) ................................. 2005-245800

(51) Int. Cl.
*H01L 27/00* (2006.01)
(52) U.S. Cl. .................................... 250/208.1; 250/216
(58) Field of Classification Search .................. 250/239, 250/216, 208.1, 221; 362/31, 27, 84, 331, 362/561
See application file for complete search history.

(56) References Cited

U.S. PATENT DOCUMENTS 5,428,468 A * 6/1995 Zimmerman et al. ........... 349/62
5,883,684 A * 3/1999 Millikan et al. ................ 349/65

FOREIGN PATENT DOCUMENTS

| JP | 06-273753 | 9/1994 |
| JP | 2000-156809 | 6/2000 |
| JP | 2000-162595 | 6/2000 |
| JP | 2001-166149 | 6/2001 |
| JP | 2002-277642 | 9/2002 |
| JP | 2002-311432 | 10/2002 |
| JP | 2003-098093 | 4/2003 |
| JP | 2004-302135 | 10/2004 |

OTHER PUBLICATIONS

Office Action from Japanese Application, dated Aug. 3, 2010, 2 pages.

* cited by examiner

Primary Examiner — Que T Le

(57) ABSTRACT

The light irradiation device is provided that can reduce moire interference with a simple and low-cost arrangement without sacrificing a compact design by comprising a transparent plate 31 which has a predetermined thickness and one of whose surfaces is arranged as an object facing surface 31a to face an object W such as a product on which light is to be irradiated, multiple reflecting sections 32 that are laid out on other surface of the transparent plate 31 with forming a microscopic space S therebetween with its light reflecting surface facing a direction of the object W, a light source section 5 arranged at a position where at least a part of the emitted light is transmitted, reaches the light reflecting surface, is reflected on the light reflecting surface and is emitted from the object facing surface 31a, and an antireflection film 33 that covers the object facing surface 31a.

6 Claims, 11 Drawing Sheets

LIGHT IRRADIATION APPARATUS AND OPTICAL MEMBER HAVING MULTIPLE REFLECTING SECTIONS AND AN ANTIREFLECTION FILM

FIELD OF THE ART

This invention relates to a light irradiation device and an optical member that irradiate the light on an object such as a product, for example, in a factory and that is preferably used in case of appearance check of the object or reading a mark described on a surface of the object.

BACKGROUND ART

Conventionally, a system has been known that irradiates the light on an object such as, for example, a product so as to create a preferable lighting environment and then takes an image of the object by the use of an image-taking device such as a CCD camera so that appearance check or mark reading can be conducted automatically.

In accordance with this system, in case that the light has to be irradiated also from a direction coaxial with an observation axis of the image-taking device, conventionally a half mirror is arranged at an angle of 45 degree on the observation axis and the light is irradiated on the half mirror from a direction orthogonal to the observation axis. With this arrangement, while the light emitted from a light source is reflected on the half mirror and travels toward a direction coaxial with the observation axis and then is irradiated on the object, the light from the object reaches the image-taking device by passing the half mirror, which makes it possible to take an image of the object. However, with this arrangement, since the half mirror has to be arranged at the angle of 45 degree, a size of the system as a whole becomes bulky especially in a direction of the observation axis and it is difficult to approach the image-taking device to the object because the half mirror intervenes between the image-taking device and the object.

Then, as shown in patent document 1, the present claimed inventor has developed an innovative thin plate-shaped light irradiation device that can be inserted in a direction orthogonal to the observation axis, which makes it possible to downsize the system drastically and to take an image of the object in a closeup mode for the first time.

More concretely, the light irradiation device is so arranged that multiple microscopic reflecting members are arranged on an opposite object facing surface of a transparent plate so as to form a space between each of the reflecting members and the LED light is introduced into the transparent plate through a side surrounding end surface of the transparent plate. The light travels inside the transparent plate while being total-reflected, a part of which is reflected on the reflecting members and irradiated toward the object from the transparent plate. An image-taking device can take an image of the object without almost any influence from the reflecting members, since the reflecting members will not fundamentally be an obstacle to taking an image like we can see a bright room through a screen.

Patent document 1: Japan patent laid open number 2003-98093

DISCLOSURE OF THE INVENTION

Problems to be Solved by the Invention

However, in case of using this light irradiation device, depending on a magnification ratio of the image-taking device, there might be a case that moire interference (interference stripes) occurs on a screen showing the image, resulting in exerting an influence on the inspection. In order to reduce the moire interference, a method wherein, for example, reflecting members are arranged in an uneven pitch or a shape of the reflecting member is made in an irregular shape, is described in the patent document 1 however, in accordance with this method, a manufacturing cost is increased more than expected.

Then the present claimed invention intends to reduce the moire interference for this kind of light irradiation device with a simple and low-cost arrangement without sacrificing a compact design.

Means to Solve the Problems

More specifically, the light irradiation device in accordance with this invention comprises a light permeable plate which has a predetermined thickness and one of whose surfaces is arranged as an object facing surface to face an object such as a product on which light is to be irradiated, multiple reflecting sections that are laid out on other surface (also be called as an opposite object facing surface) of the light permeable plate with forming a microscopic space therebetween with its light reflecting surface facing a direction of the object, a light source section arranged at a position where at least a part of the emitted light is transmitted inside the light permeable plate, reaches the light reflecting surface, is reflected on the light reflecting surface and is emitted from the object facing surface, and an antireflection film that covers the object facing surface.

In addition, the present claimed invention is related with an optical member separately arranged from the light source, and the optical member is characterized by comprising a light permeable plate which has a predetermined thickness and one of whose surfaces is arranged as an object facing surface to face an object such as a product on which light is to be irradiated, multiple reflecting sections that are laid out on an opposite object facing surface of the light permeable plate with forming a microscopic space therebetween with its light reflecting surface facing a direction of the object, and an antireflection film that covers the object facing surface.

The meaning of "Reflection" here is basically diffuse reflection (scattered reflection), and includes also regular reflection in some cases.

In consequence of keen examination, the present claimed inventor has found out that the moire interference is caused by that a part of the light is reflected on each reflecting section and travels toward the object and then is reflected again on the object facing surface and travels toward the image-taking device. More specifically, the present claimed invention is based on this clarified fact of the reflecting section, and makes it possible to reduce the moire interference by restraining the light that is reflected on the object facing surface and travels toward the image-taking device with a simple and low-cost structure wherein an antireflection film is arranged.

As a concrete structure of the light source section represented is that the light source section is arranged to front a side surrounding end surface of the light permeable plate and comprises multiple LEDs that introduce the light into inside of the light permeable plate from the side surrounding end surface.

In view of a production cost, it is preferable that the reflecting sections are laid out longitudinally and transversely. However, as mentioned above, if an image-taking device has multiple picture elements laid out at a predetermined pitch longitudinally and transversely respectively like a CCD camera, the moire interference occurs at a certain imaging magnification when the layout direction of the picture elements is substantially aligned with the layout direction of the reflecting sections or the layout direction of the picture elements is at a predetermined angle with the layout direction of the reflection sections.

It is a matter of course that the moire interference can be repressed by the use of the antireflection film, however, in order to further improve an effect of repressing the moire interference, it is preferable that an angle θ between a longitudinal layout direction of the picture elements and a longitudinal layout direction of the reflecting sections is set at an angle evading the vicinity of 0°, α, 90°−α, and 90° in a normal layout posture relative to the image-taking device. In this regard, tan α=transversal layout pitch of the reflecting sections/longitudinal layout pitch of the reflecting sections, and transversal layout pitch≦longitudinal layout pitch.

More concretely, it is preferable that the angle θ is about 5°~10°≦θ≦α−10°~α5°, α+5°~α+10°≦θ≦80°−α~85°−α, or 95°−α~10°−α≦θ≦80°~85°.

If the angle is set θ, the interference stripes become fainter and their pitches become extremely small, thereby being vanishingly visible.

In case that the reflecting sections are laid out at generally even pitch longitudinally and transversely (in case α=45°), it is further preferable that the angle θ is about 22.5° or 67.5°.

EFFECT OF THE INVENTION

With the light irradiation device having the above arrangement in accordance with the present claimed invention, it is possible to effectively repress the moire interference with a very simple and low-cost structure wherein the object facing surface is covered with the antireflection film while taking advantage of the characteristics that it is possible to take an image of the object in a closeup mode with a compact structure.

EXPLANATION OF THE CODES

Figure 1:
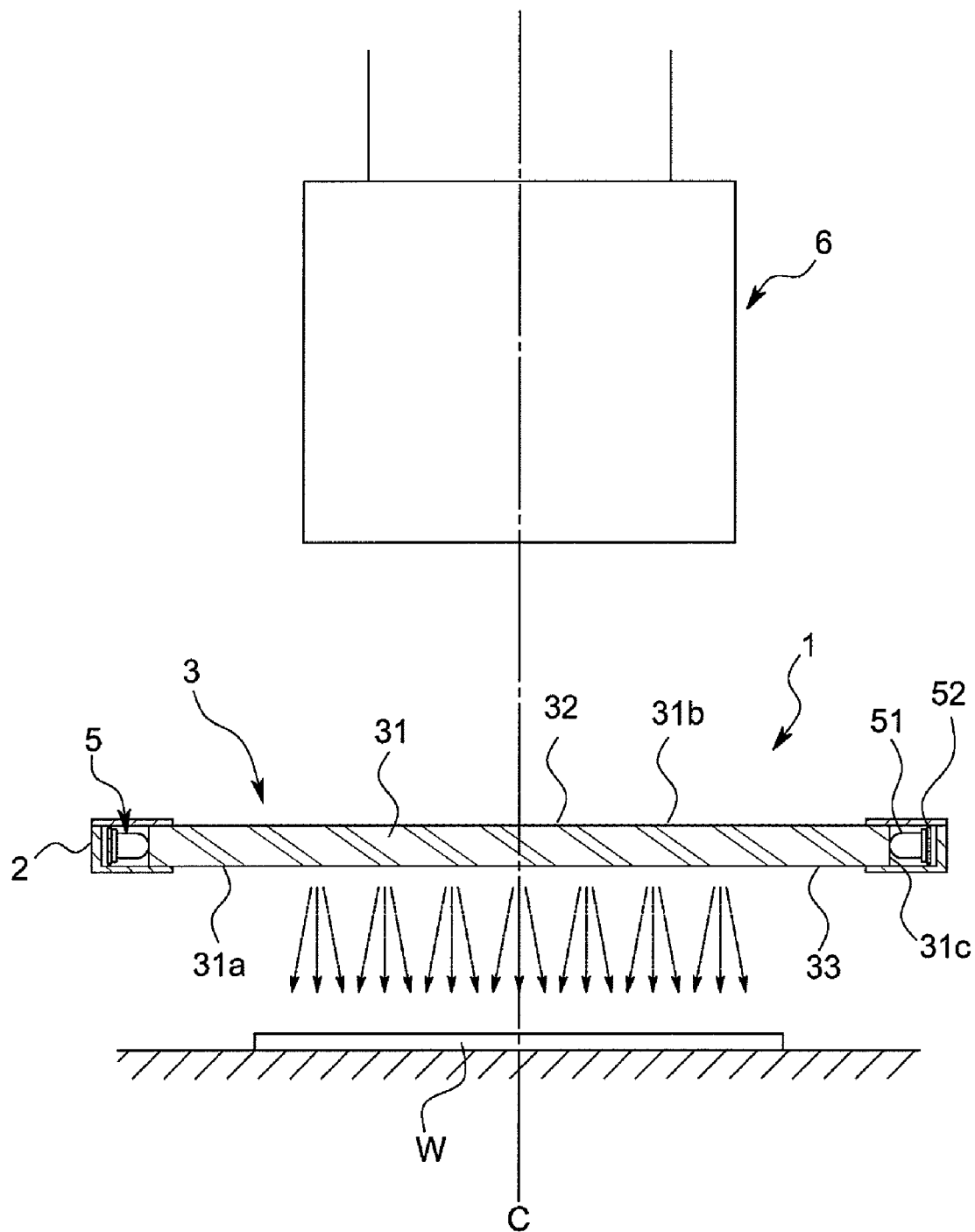
FIG. 1 is a central longitudinal front end view showing an internal structure of a light irradiation device in accordance with one embodiment of the present claimed invention.

1 . . . light irradiation device
3 . . . optical member
31 . . . transparent (light permeable) plate
31a . . . one surface (object facing surface)
31b . . . other surface (opposite object facing surface)
31c . . . side surrounding surface
32 . . . reflecting sections
33 . . . antireflection film
5 . . . light source section
51 . . . LED
6 . . . image-taking device (CCD camera)
S . . . space
W . . . object

BEST MODES OF EMBODYING THE INVENTION

One embodiment of the present claimed invention will be explained with reference to drawings.

Figure 2:
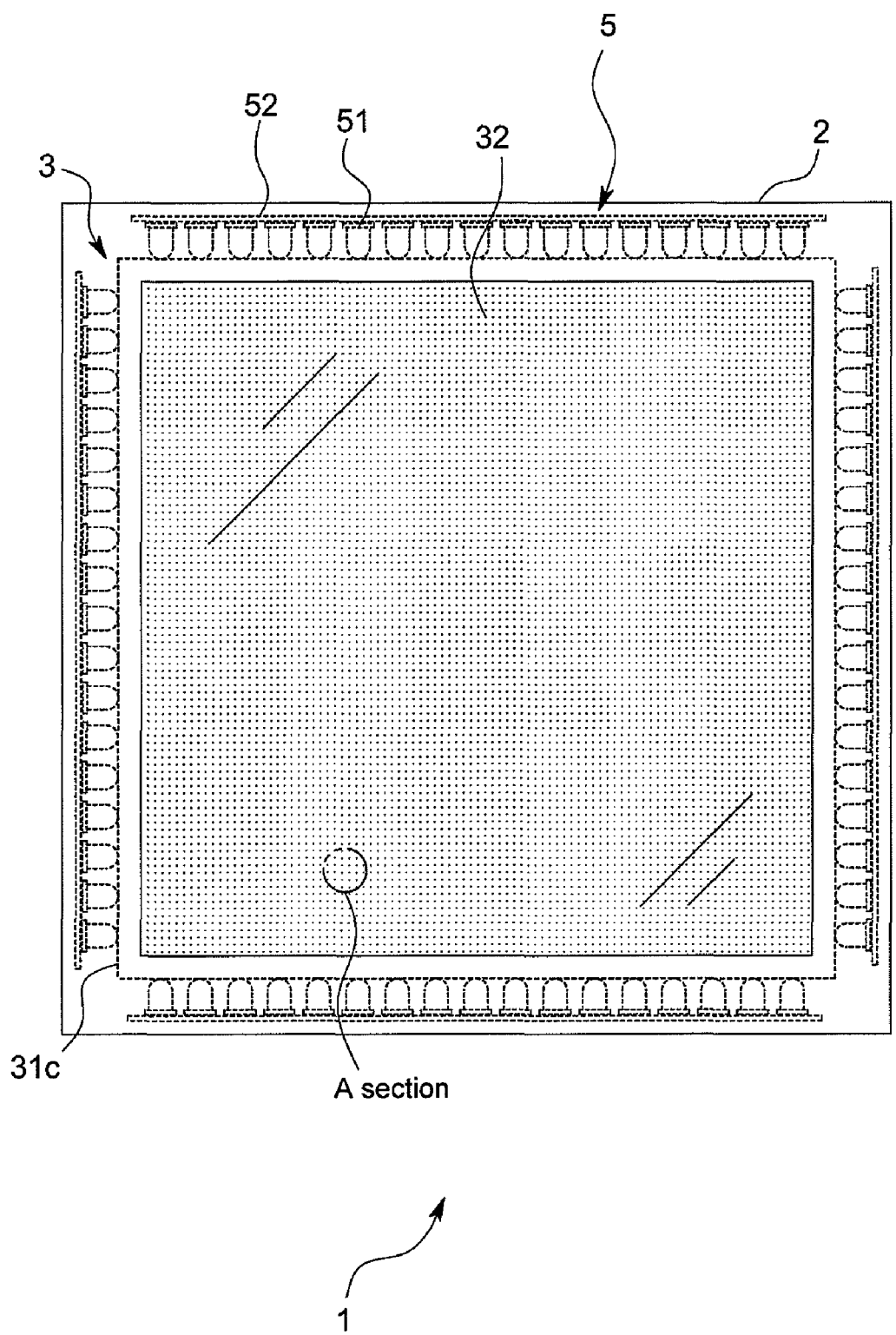
FIG. 2 is a plane view of the light irradiation device in accordance with this embodiment.

A light irradiation device 1 in accordance with this embodiment is, as shown in FIG. 1 and FIG. 2, in a thin plate shape as a whole, and arranged on an image-taking axis C between an object W and an image-taking device 6 orthogonally to the image-taking axis C. The light irradiation device 1 illuminates the object W and makes it possible for the image-taking device 6 to take an image of the object W by transmitting a part of the light from the object W.

Concretely, the light irradiation device 1 comprises a platy rectangular optical member 3, a light source section 5 that irradiates the light from a side surrounding of the optical member 3 and a frame body 2 that holds the optical member 3 and the light source section 5.

Figure 3:
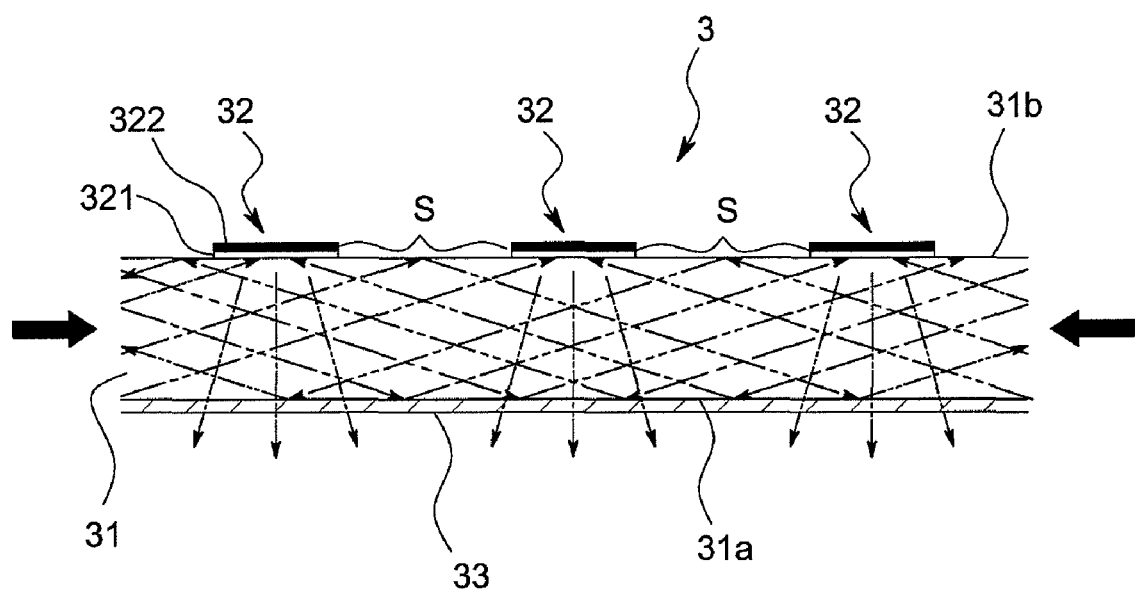
FIG. 3 is a partially enlarged longitudinal front end view mainly showing a reflecting section of the light irradiation device in accordance with this embodiment.

The optical member 3, especially as shown in FIG. 3, comprises a transparent (light permeable) plate 31 one of whose surfaces as being an object facing surface 31a is arranged to face the object W such as a product on which light is to be irradiated, multiple reflecting sections 32 that are laid out on other surface (opposite object facing surface) 31b of the transparent plate 31, and an antireflection film 33 that covers the object facing surface 31a.

The transparent plate 31 is of a transparent and colorless plate form having an equal thickness and of a square shape in a plane view, for example, made of a material such as acrylic or glass.

Figure 4:
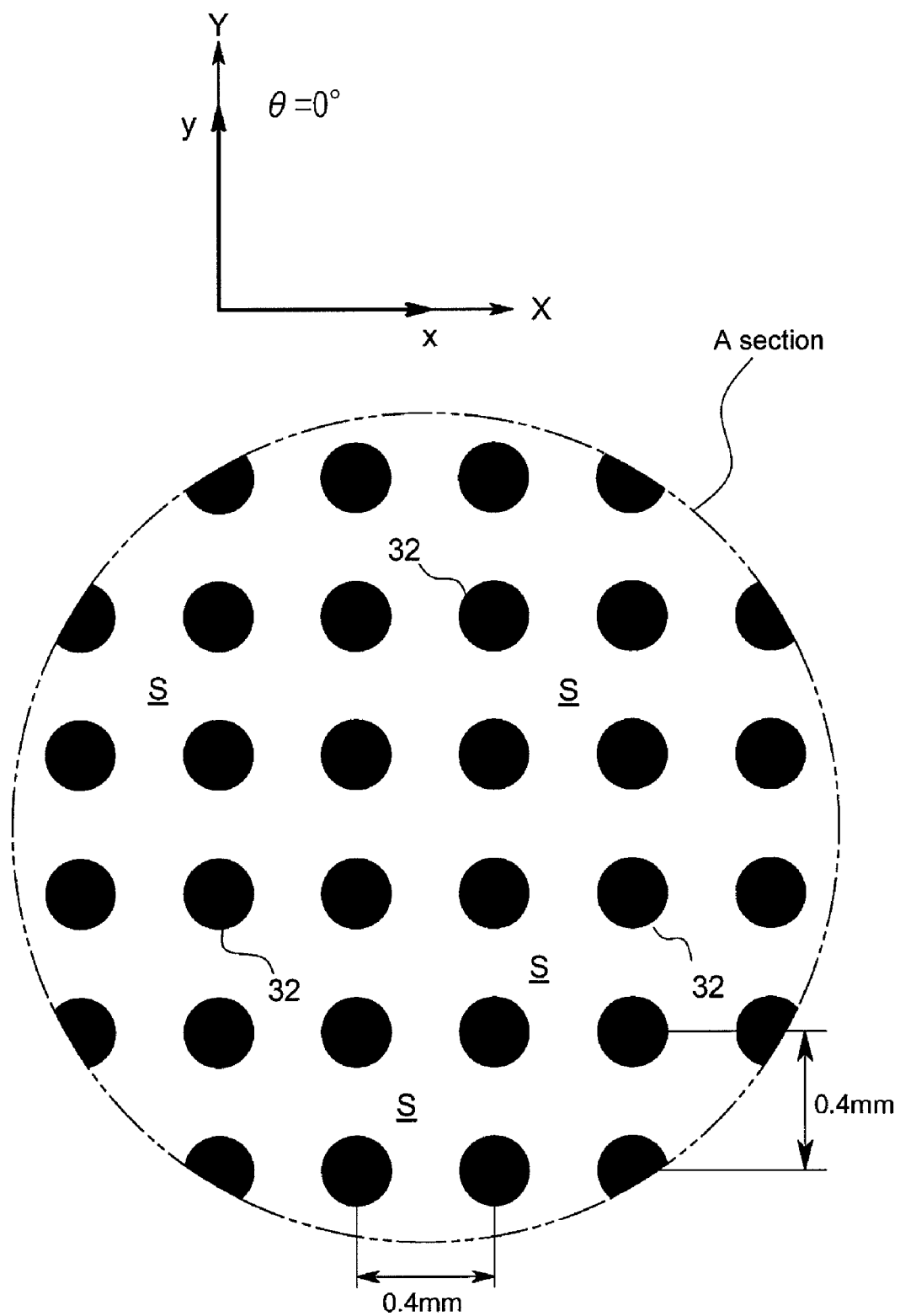
FIG. 4 is a detail view of A section in FIG. 2.

The reflecting sections 32 are, as shown in FIG. 3 and FIG. 4, of a dual structure comprising a reflecting layer 321 that reflects the light diffusely and a light shadowing layer 322 that rarely reflects the light, each of which is extremely small and thin and in a circular form in a plane view, with a diameter of several dozen~several hundred μm and a thickness of a micron order. Then the multiple reflecting sections 32 are laid out longitudinally and transversely at an equal pitch (for example, about 0.4 mm pitch) across a substantial area except for a side peripheral edge section of the opposite object facing surface 31b of the transparent plate 31. In addition, each reflecting section 32 is attached to the opposite object facing surface 31b of the transparent plate 31 so that the reflecting layer 321 faces a direction of the object W. FIG. 3 is a pattern diagram for better understanding, wherein a thickness of the reflecting section 32 is exaggerated and a thickness of the transparent 31 is expressed thinner than an actual thickness. The reflecting layer 321 is formed with, for example, a white pigment containing a particulate reflecting filler (not shown in drawings) as being a light diffusion member, and the light reflecting surface as being a surface of the reflecting layer 321 reflects mainly the light and a part of the light coming inside of the reflecting layer 321 is diffused and reflected on the reflecting filler. On the while, the light shadowing layer 322 is formed with a matte black (for example, brown or gray)

material such as chrome oxide ($CrO_2$). In this embodiment, a thin chrome layer of mirror finished (not shown in drawings) is further arranged between the light shadowing layer 322 and the reflecting layer 321 for the purpose of reflecting the light that passes the reflecting layer 321.

The antireflection film 33 is formed with, for example, a multi-layer film, and has a function to restrain reflection of the incoming light and to improve the transmissivity.

The light source section 5 comprises four units, each of which corresponds to each of four side surrounding end surfaces 31c of the transparent plate 31 respectively. Each unit comprises a strip-shaped substrate 52 and multiple LEDs 51 loaded on the substrate 52 on a line at even intervals, and the LEDs 51 are arranged to front the side surrounding end surface 31c of the transparent plate 31 and the light is irradiated toward inside of the transparent plate 31 through the side surrounding end surface 31c.

The frame body 2 is in a looped rectangle (square) made of metal having a surrounding groove that opens into an inner peripheral surface, and accommodates the light source section 5 in its surrounding groove. In addition, the side surrounding edge section of the transparent plate 31 is held in a direction of its thickness by an opening edge of the groove.

Next, an operation of the light irradiation device 1 of the above arrangement will be explained as follows.

First, as shown in FIG. 1, the object W is set to face the image-taking device 6. During this process, the light irradiation device 1 is placed on the image-taking axis C so that the object facing surface 31a faces the object W.

With this state kept, when the light is irradiated by the light source section 5, the light enters inside of the side surrounding end surface 31c of the transparent plate 31, and then as shown in FIG. 3, travels toward a center portion while being totally reflected between the object facing surface 31a and the opposite object facing surface 31b. During this progress, the light that reaches the reflecting sections 32 attached to the object facing surface 31a is scatter-reflected on the reflecting sections 32, goes out through the object facing surface 31a as the homogenized scattered light and then is irradiated toward the object W. The object W is illuminated uniformly.

The image-taking device 6 takes an image of the object W as mentioned above by acquiring the light that is reflected on the object W and that passes the transparent plate 31 through the spaces S between the reflecting sections 32 so as to inspect a surface of the object W or to read a mark on the object W. Since the reflecting sections 32 are microscopic, the reflecting sections 32 will not fundamentally be an obstacle to taking an image like we can see a bright room through a screen. However, it is more preferable that a size or a pitch of the spaces S or the reflecting sections 32 is optimally determined with a distance between the image-taking device 6 and the reflecting sections 32 or a distance between the image-taking device 6 and the object W set as a parameter. For example, in case that the distance between the image-taking device 6 and the reflecting sections 32 is short, a size or a pitch of the space S or the reflecting sections 32 may be set big properly, and vice versa.

As mentioned, it is possible to illuminate the object W from a coaxial direction of the monitoring axis C of the image-taking device 6 by means of the reflecting light on the reflecting sections 32 and to conduct inspection by taking an image of the object W through the spaces S by the use of the image-taking device 6.

In case that a longitudinal (or transversal) layout pitch of the picture elements is substantially uniform like the CCD camera as being the image-taking device 6 of this embodiment, moire interference might occur on the taken image. As long as the present claimed inventor has found out, a cause for the moire interference is "the light that is reflected on the reflecting sections 32 and travels toward the object W, and then is reflected again on the object facing surface 31a and travels toward the image-taking device 6". More specifically, the moire interference occurs at a time when each reflecting section 32 that is reflected on the picture elements by "the light" substantially overlaps each picture element.

More specific explanation is as follows. In this embodiment, as shown in FIG. 4, for example, the longitudinal layout direction Y (or the transversal layout direction X) of the picture elements is substantially aligned with the longitudinal layout direction y (or the transversal layout direction x) of the reflecting sections 32 (an angle $\theta$ between the longitudinal layout direction Y and the longitudinal layout direction y is approximately 0°). If an image is taken with a magnification wherein the apparent longitudinal direction layout pitch that is reflected on the picture elements of the reflecting sections 32 is substantially aligned with the longitudinal direction layout pitch of the picture elements, the light interferes and moire interference occurs. More specifically, in case that the pitch of the reflecting sections 32 is 400 μm and the pitch of the picture elements is 9 μm, if the imaging magnification is set around 9/400, each reflecting section 32 that is reflected on the picture elements substantially overlaps each picture element so that moire interference occurs.

Figure 5:
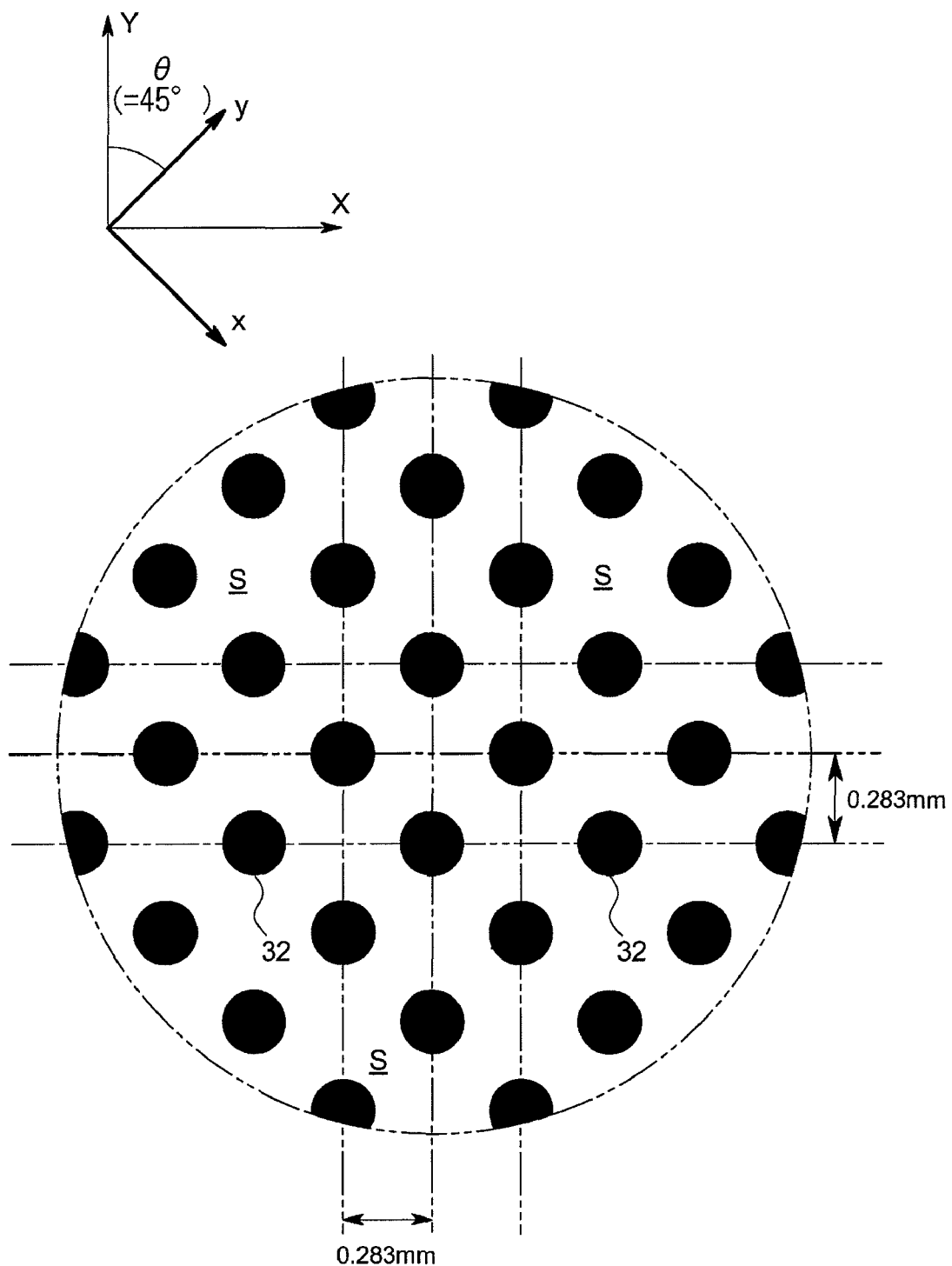
FIG. 5 is a partially enlarged plane view showing a case when a layout direction of the reflecting sections is changed.

In addition, the angle $\theta$ at a time when the moire interference occurs is not limited to 0° but also 90°. In case that the longitudinal and transversal layout pitch of the reflecting sections 32 is substantially the same like this embodiment, the moire interference occurs when the angle $\theta$ is also around 45°. The reason why the moire interference occurs at a time when the imaging magnification is set around 9/283 is that the reflecting sections 32 are aligned at a pitch of 283 μm in the longitudinal (transversal) layout direction Y (X) in view of the longitudinal (transversal) layout direction Y (X) of the picture elements as shown in FIG. 5.

Then in accordance with this embodiment, it is possible to reduce "the light that is reflected on the reflecting sections 32 and travels toward the object W, and then is reflected again on the object facing surface 31a and travels toward the image-taking device 6" that would be a cause of the above-mentioned moire interference with a simple and low-cost arrangement wherein the antireflection film 33 is provided on the object facing surface 31a, resulting in restraining the moire interference drastically.

The present claimed invention is not limited to the above-mentioned embodiment.

As mentioned above, the angle $\theta$ at which the moire interference significantly occurs is in the vicinity of 0°, 45° and 90° in case that the longitudinal and transversal layout pitches of the reflecting sections 32 are substantially the same. As a result, it is possible to reduce the moire interference if the layout direction of the reflecting sections 32 is determined with avoiding these angles.

A generalized explanation will be made in order to make it possible to apply the explanation to a case wherein the pitch of the longitudinal direction of the reflecting sections 32 is different from the pitch of the transversal direction of the reflecting sections 32. The angle at which the moire interference occurs significantly is 0°, $\alpha$, 90°−$\alpha$, 90° at a time when the pitch of the longitudinal direction of the reflecting sections 32 is p and the pitch of the transversal direction thereof is q. Where, $\alpha$ is an angle determined by $\tan \alpha = q/p$, and $p \geq q > 0$ (The reason why p is bigger than or equal to q is that a lengthy direction is defined as the longitudinal direction).

Figure 6:
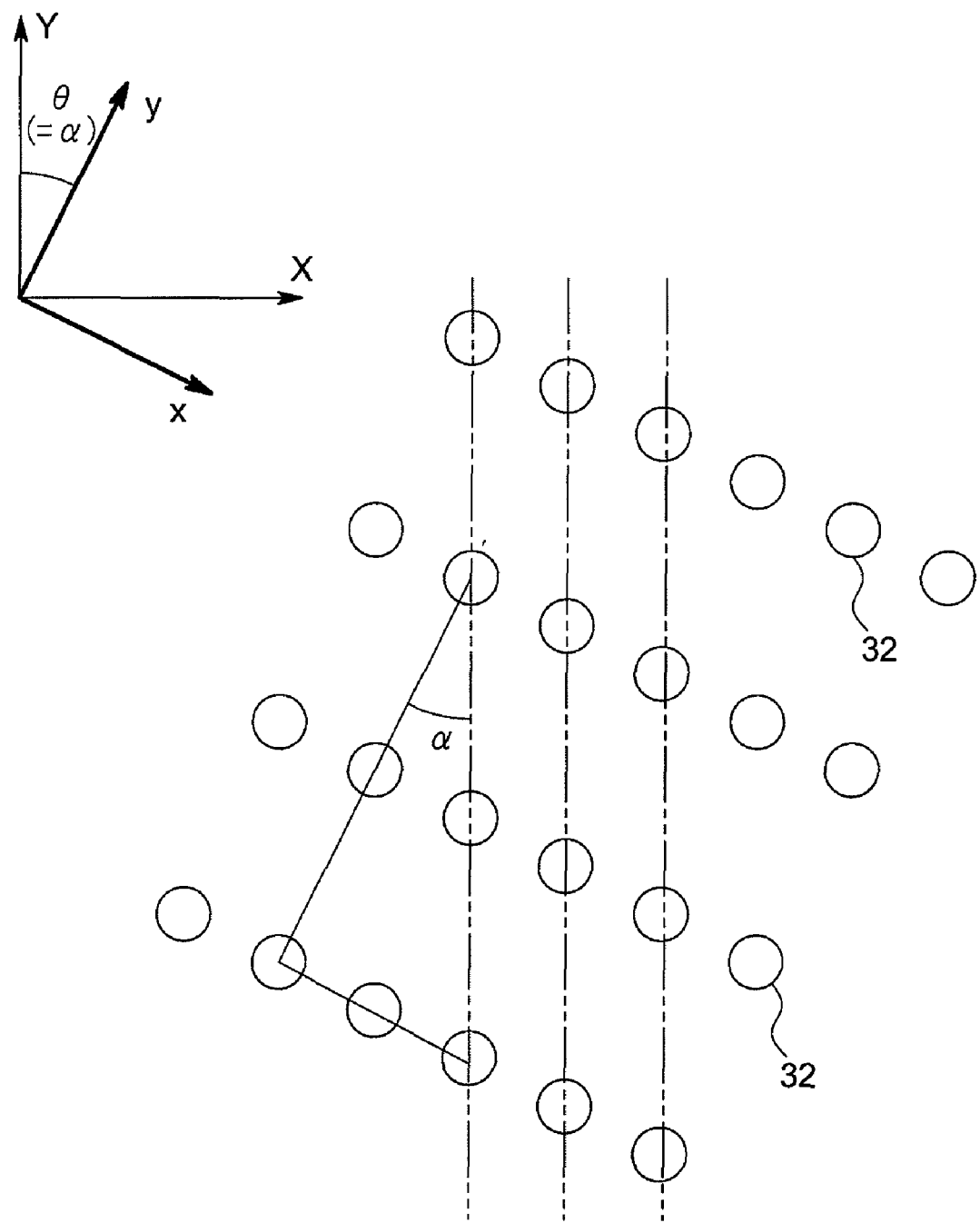
FIG. 6 is a phenomenon explanatory view showing a layout direction of picture elements in case that moire interference occurs.
Figure 7:
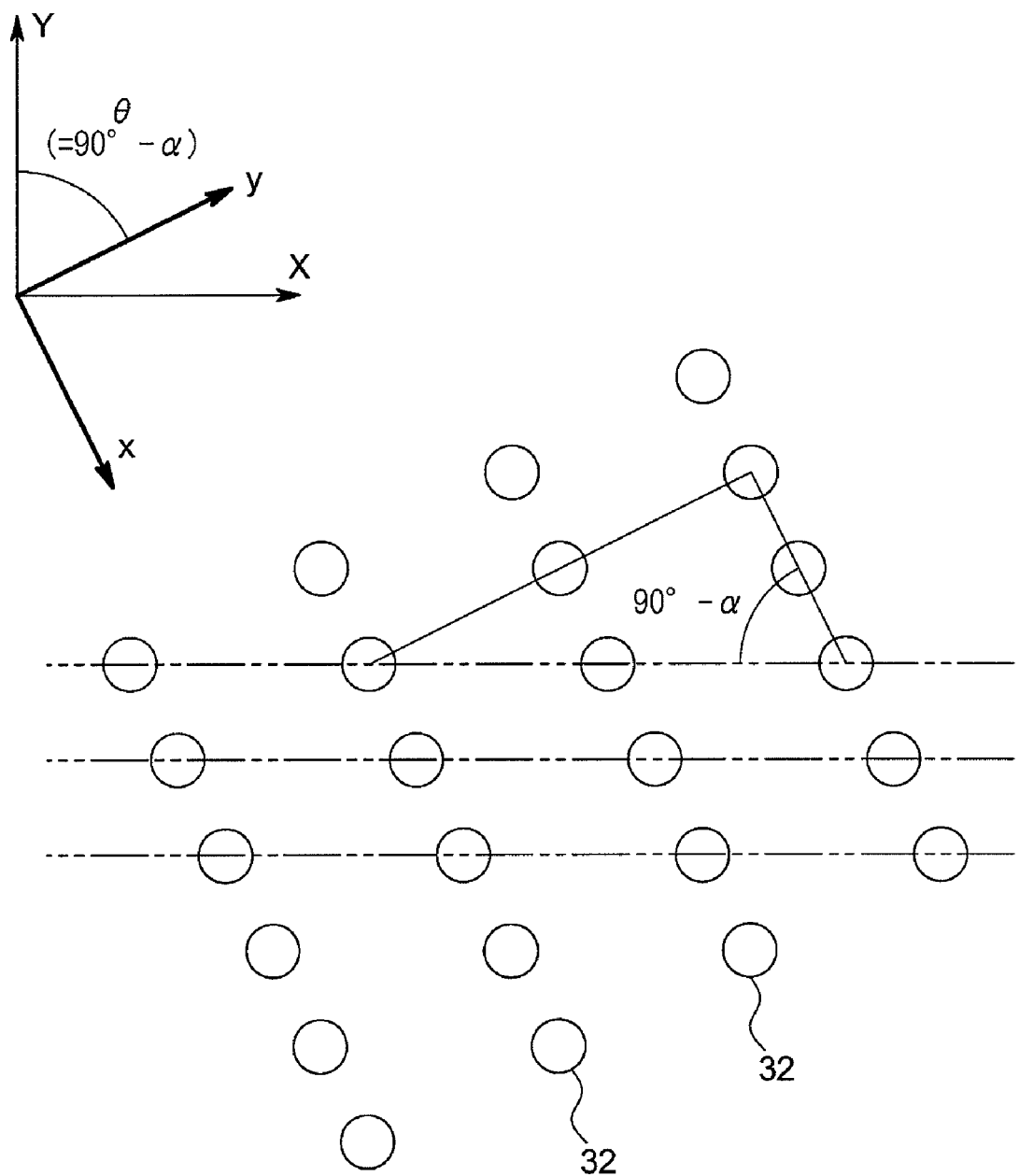
FIG. 7 is a phenomenon explanatory view showing a layout direction of picture elements in case that moire interference occurs.

Not only 0° and 90° but also α and 90°−α represent an angle of a diagonal line of the lattice-arranged reflecting sections 32, and at a time when θ is set at 0°, α, 90°−α and 90°, the diagonal line is aligned with the layout direction Y (or X) of the picture elements and the reflecting sections 32 are aligned in the same direction as the layout direction Y (or X) of the picture elements as shown in FIG. 6 and FIG. 7.

As a result, it is possible to reduce the moire interference if the layout direction of the reflecting sections 32 is determined by avoiding the angles smaller and bigger than these angle (0°, α, 90°−α, 90°) by 5°~10°.

More specifically, the angle θ may be within either one of the ranges.
(1) 5°~10°≦θ≦α−10°~α−5°
(2) α+5°~α+10°≦θ≦80°−α~85−α
(3) 95°−α~100°−α≦θ≦80°~85°

Figure 8:
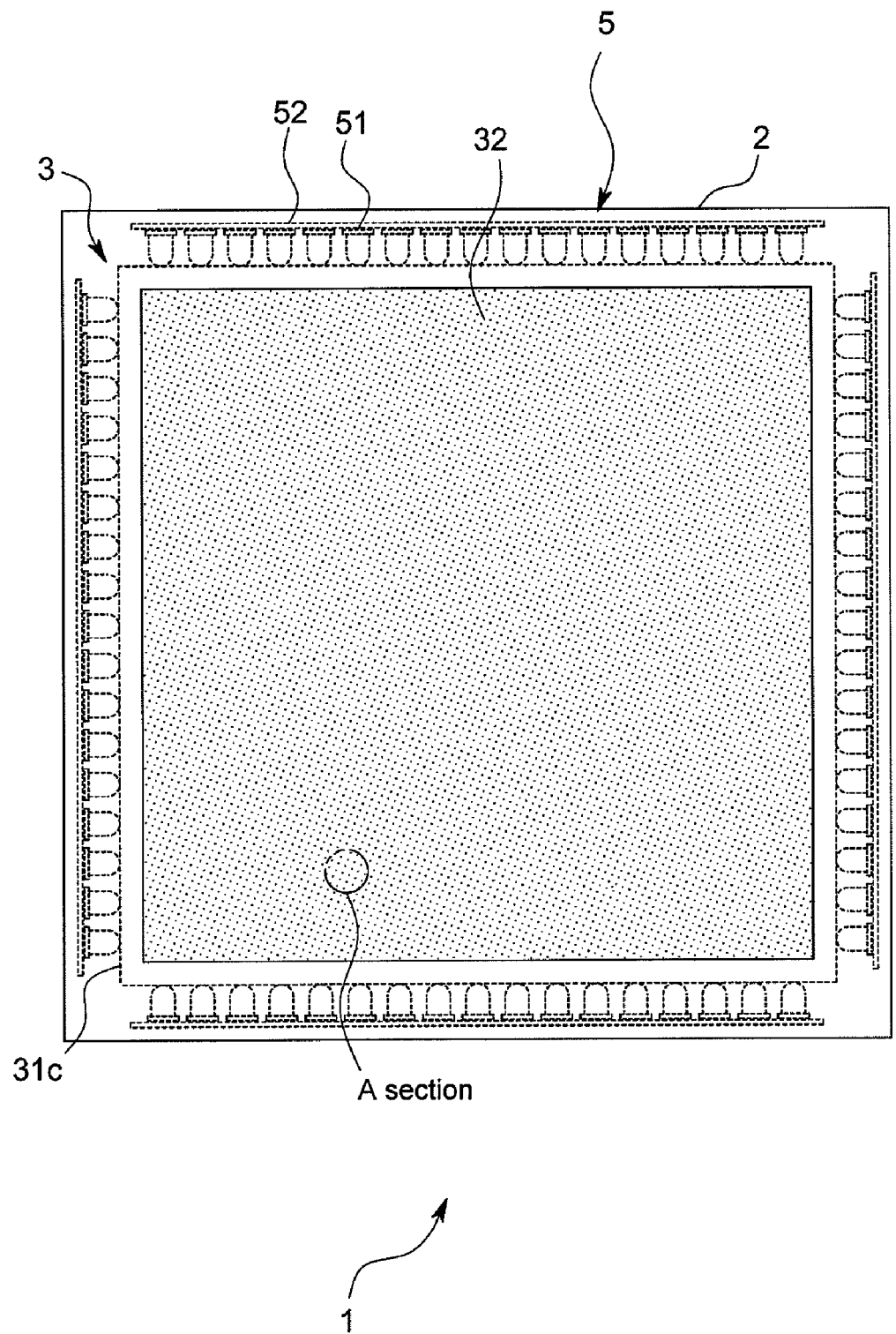
FIG. 8 is a central longitudinal front end view showing an internal structure of a light irradiation device in accordance with another embodiment of the present claimed invention.
Figure 9:
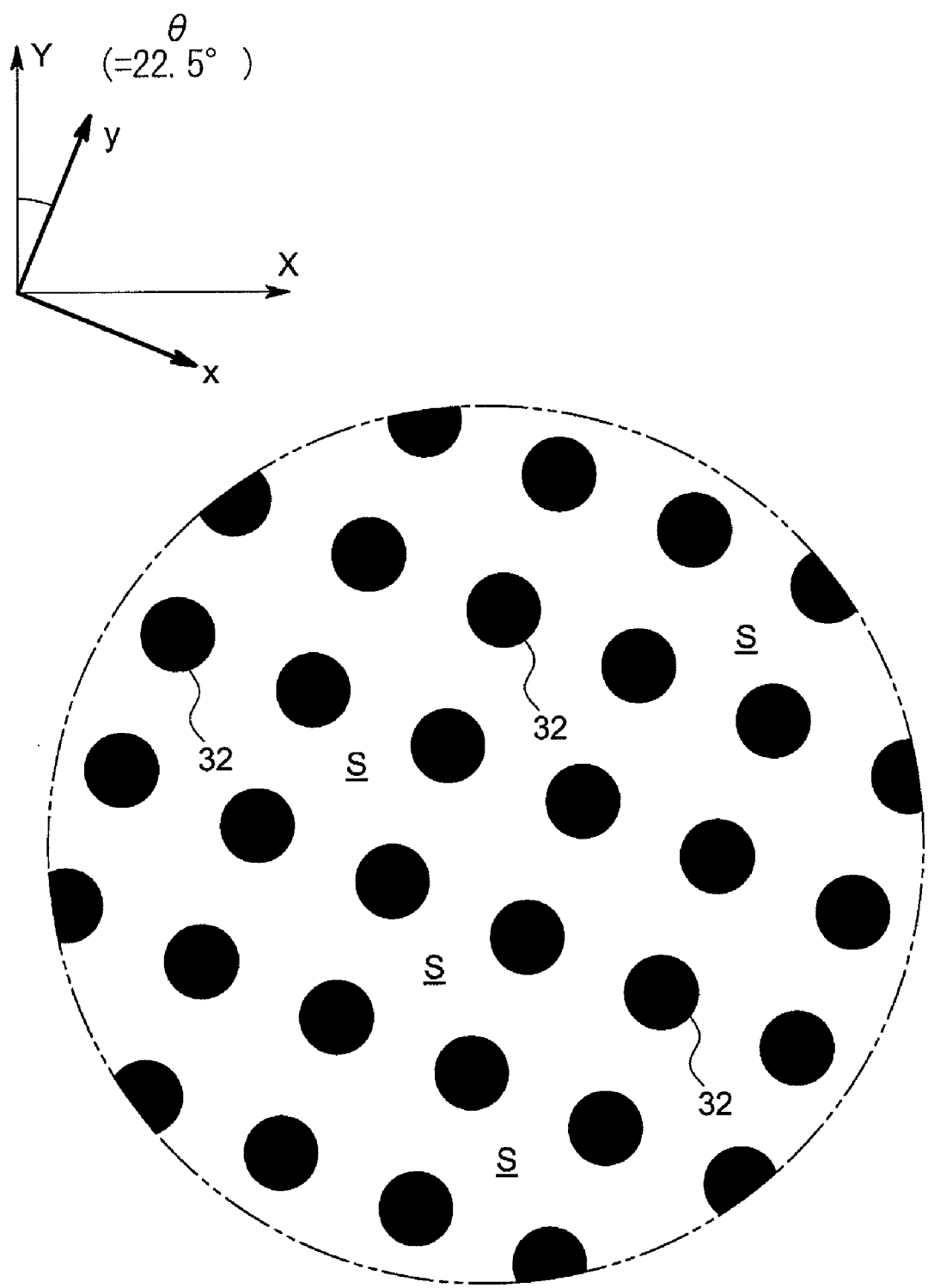
FIG. 9 is a detail view of A section in FIG. 8.

Then in this modified embodiment, as shown in FIG. 8 and FIG. 9, a posture indicating section showing a normal layout posture is arranged in the light irradiation device 1 and the angle θ can be set within the above-mentioned range by setting a posture of the light irradiation device 1 relative to the image-taking device 6 to be the normal layout posture based on the posture indicating section.

More concretely, the posture indicating section is a side of the frame body 2. For the light irradiation device 1 wherein the longitudinal and transversal layout pitches of the reflecting sections 32 are substantially the same, the longitudinal layout direction y of the reflecting sections 32 is set at an angle (θ=22.5°) relative to this side. As a result, if the side of the frame body 2 is arranged appropriately relative to the image-taking device 6, the angle θ between the longitudinal (or transversal) layout direction of the picture elements and the longitudinal (or transversal) layout direction of the reflecting sections 32 can be set accurately.

Figure 10:
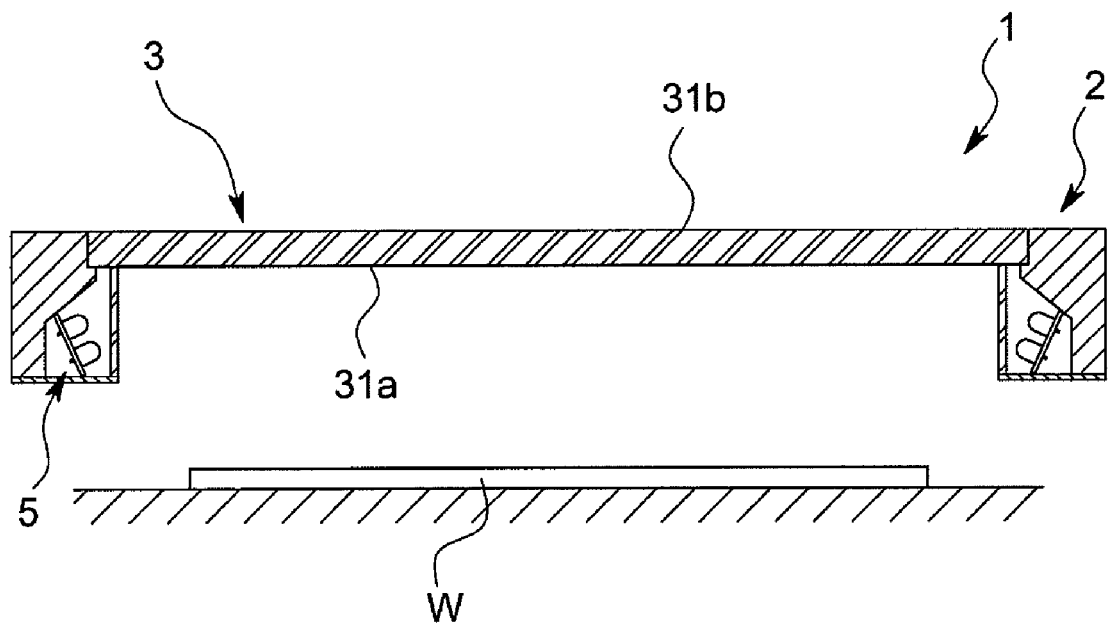
FIG. 10 is a central longitudinal front end view showing a light irradiation device in accordance with further different embodiment of the present claimed invention.

In addition, as shown in FIG. 10, the light may be emitted not from the side surrounding end surface 31c of the transparent plate 31 but from the object facing surface 31a at an angle so as to reach the reflecting sections 32.

Furthermore, the transparent plate is not limited to a flat plate, and may be a curved plate such as a spherical shape.

Figure 11:
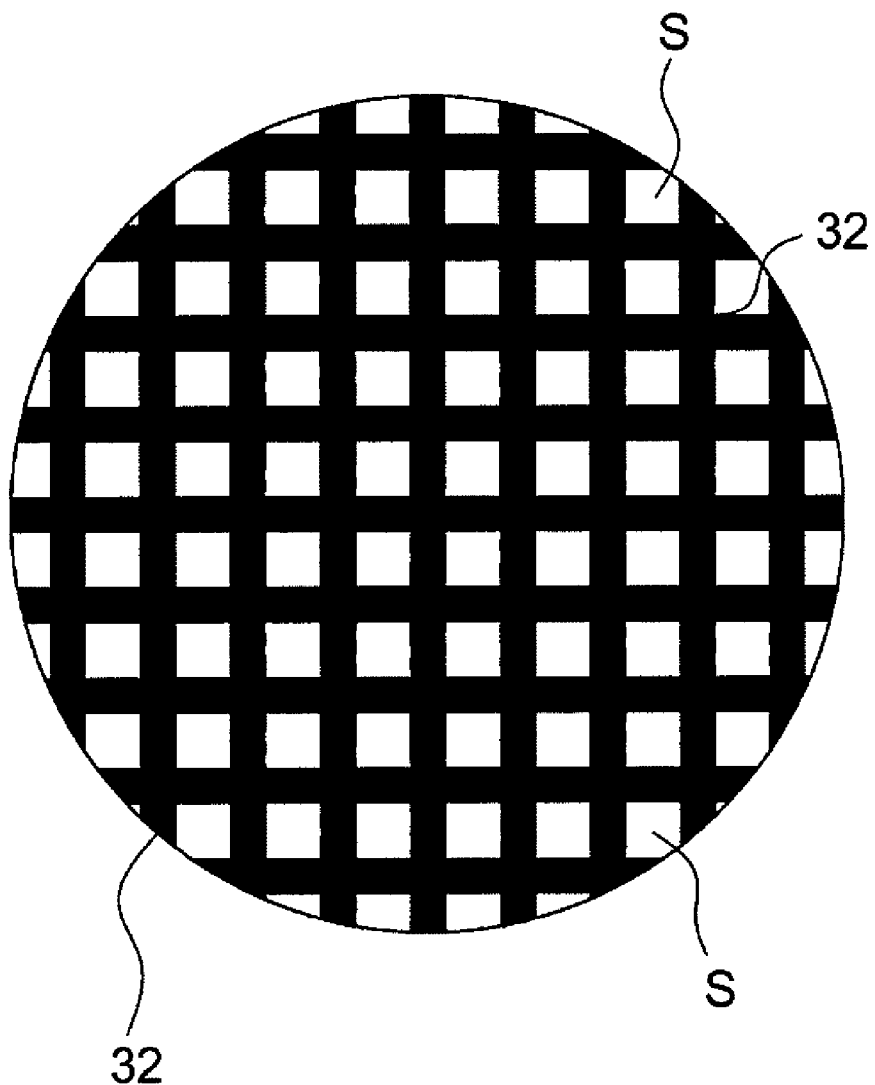
FIG. 11 is a partially enlarged plane view of reflecting sections in accordance with further different embodiment of the present claimed invention.

In addition, as shown in FIG. 11, each reflecting sections 32 may be continuously arranged in a sheet-like mesh form so as to make the spaces S between the meshes.

The present claimed invention is not limited to the above-mentioned illustrated embodiment and the above-mentioned explanatory embodiment, and it is a matter of course each component may be appropriately combined and variously modified without departing from the spirit of the invention.

POSSIBLE APPLICATIONS IN INDUSTRY

The light irradiation device in accordance with the present claimed invention of the above arrangement can reduce the moire interference with a simple and low-cost arrangement without sacrificing a compact design.

The invention claimed is:

1. An inspection device comprising:
a light irradiation device which comprises:
a light permeable plate which has a predetermined thickness with one surface arranged as an object facing surface to face an object on which light is to be irradiated such as a product,
multiple reflecting sections that are laid out on another surface of the light permeable plate and forming a microscopic space therebetween with the multiple reflecting sections providing light reflecting surfaces facing in a direction of the object,
a light source section arranged at a position where at least a part of the emitted light is transmitted into the light permeable plate, reaches the light reflecting surfaces and is reflected on the light reflecting surfaces to be emitted from the object facing surface,
an antireflection film that covers the object facing surface, and
an image-taking device which takes an image of the object by acquiring the light that is reflected on the object and that passes the on the light permeable plate the spaces between the multiple reflecting sections, wherein
the light irradiation device is arranged between the object and the image-taking device, and
the antireflection film reduces the light that is reflected on the multiple reflecting sections and travels toward the object, and then is reflected again on the object facing surface to restrain any moiré interference.

2. The inspection device described in claim 1, wherein the light source section is arranged to front a side surrounding end surface of the light permeable plate and comprises multiple LEDs that introduce the light into inside of the light permeable plate from the side surrounding end surface.

3. The inspection device described in claim 1 wherein the image-taking device has multiple picture elements laid out at a predetermined pitch longitudinally and transversely respectively, and
the multiple reflecting sections are laid out longitudinally and transversely, a normal layout posture relative to the image-taking device is determined and an angle θ between a longitudinal layout direction of the picture elements and a longitudinal layout direction of the reflecting sections is set at an angle evading the vicinity of 0°, α, 90°−α, and 90° when the light irradiation device takes the normal layout posture, wherein
α is an angle shown by tan α=transversal layout pitch of the reflecting sections/longitudinal layout pitch of the multiple reflecting sections, and transversal layout pitch≦longitudinal layout pitch.

4. The inspection device described in claim 3, wherein the angle θ is selected from the group consisting of about 10°≦θ≦about α−10°, about α+10°≦θ≦about 80°−α, and about 100°−α≦θ≦about 80°.

5. The inspection device described in claim 3, wherein the angle θ is about 22.5° in the case that the multiple reflecting sections are laid out at generally an even pitch, longitudinally and transversely.

6. The inspection device described in claim 4, wherein the angle θ is about 22.5° in the case that the multiple reflecting sections are laid out at generally an even pitch, longitudinally and transversely.

* * * * *